(12) United States Patent
Sadek

(10) Patent No.: US 11,260,177 B1
(45) Date of Patent: Mar. 1, 2022

(54) DENTAL ANESTHETIC BUFFER SYSTEM

(71) Applicant: Yasser Sadek, San Diego, CA (US)

(72) Inventor: Yasser Sadek, San Diego, CA (US)

(*) Notice: Subject to any disclaimer, the term of this patent is extended or adjusted under 35 U.S.C. 154(b) by 1142 days.

(21) Appl. No.: 14/662,231

(22) Filed: Mar. 18, 2015

Related U.S. Application Data

(60) Provisional application No. 61/954,628, filed on Mar. 18, 2014.

(51) Int. Cl.
*A61M 5/24* (2006.01)
*A61M 19/00* (2006.01)

(52) U.S. Cl.
CPC ........ *A61M 5/2448* (2013.01); *A61M 5/2429* (2013.01); *A61M 19/00* (2013.01); *A61M 2202/048* (2013.01)

(58) Field of Classification Search
CPC .............. A61M 5/2448; A61M 5/2455; A61M 5/2466; A61M 5/284; A61M 5/285; A61M 5/286; A61M 5/2429; A61M 2005/2462; A61M 2005/247; A61M 2005/2474; A61M 2005/287; A61M 19/00; A61M 2202/048
See application file for complete search history.

(56) References Cited

U.S. PATENT DOCUMENTS

| | | | | |
|---|---|---|---|---|
| 2,705,956 A | * | 4/1955 | McLaughlin | A61D 19/027 604/404 |
| 3,595,439 A | * | 7/1971 | Newby | A61C 5/66 222/80 |
| 3,718,139 A | * | 2/1973 | Hanford | A61M 5/31596 604/87 |
| 3,756,390 A | * | 9/1973 | Abbey | A61M 5/284 206/219 |
| 4,648,532 A | * | 3/1987 | Green | A61C 5/66 206/222 |
| 5,114,240 A | * | 5/1992 | Kindt-Larsen | A61B 17/8816 222/129 |
| 5,137,511 A | * | 8/1992 | Reynolds | A61M 5/284 604/191 |
| 5,137,528 A | * | 8/1992 | Crose | A61M 5/2448 222/327 |
| 5,791,466 A | * | 8/1998 | Tsals | A61J 1/2089 206/222 |
| 7,748,526 B2 | * | 7/2010 | Iwatschenko | B65D 81/3255 206/219 |
| 8,911,395 B2 | * | 12/2014 | Just | A61M 5/2448 604/191 |
| 9,616,176 B2 | * | 4/2017 | Just | A61M 5/2459 |
| 9,775,690 B2 | * | 10/2017 | Cheetham | A61C 9/0026 |

(Continued)

*Primary Examiner* — Bradley J Osinski
(74) *Attorney, Agent, or Firm* — Law Office of Glenn Smith; Glenn R. Smith; Lisa L. Smith

(57) ABSTRACT

A dental anesthetic buffer system has a carpule having a first end and a second end, a capsule at least partially disposed within the carpule proximate the first end so as to fluidly seal the first end, and a membrane disposed proximate the second end so as to fluidly seal the second end. A liquid anesthetic is contained within the carpule between the first end and the second end. A liquid buffer is contained within the capsule. An activator is disposed proximate the buffer and extends from the carpule first end. The activator is manually moved from a first position to a second position so as to release the buffer from the capsule and combine the buffer with the anesthetic.

7 Claims, 14 Drawing Sheets

(56) References Cited

U.S. PATENT DOCUMENTS

| | | | | |
|---|---|---|---|---|
| 2004/0092883 | A1* | 5/2004 | Casey, II | A61M 5/19 604/191 |
| 2006/0144869 | A1* | 7/2006 | Chang | A61M 5/31596 222/386 |
| 2007/0225640 | A1* | 9/2007 | Chang | A61M 5/31596 604/92 |
| 2012/0074001 | A1* | 3/2012 | Genosar | A61J 1/2089 206/219 |
| 2013/0110039 | A1* | 5/2013 | Just | A61M 5/2448 604/87 |
| 2013/0259279 | A1* | 10/2013 | Hong | H04R 25/65 381/322 |
| 2015/0165124 | A1* | 6/2015 | Just | A61M 5/2448 604/87 |

* cited by examiner

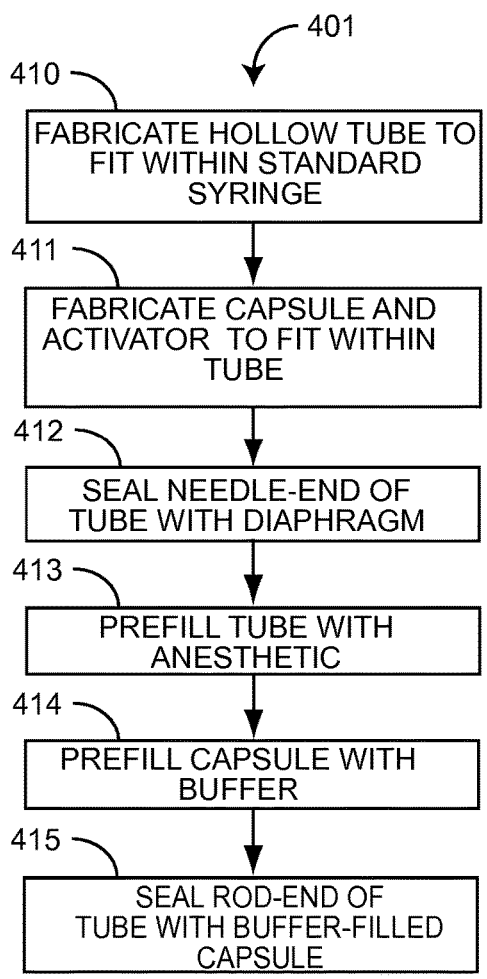
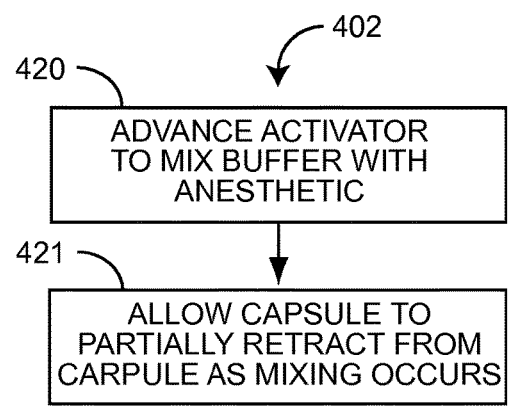
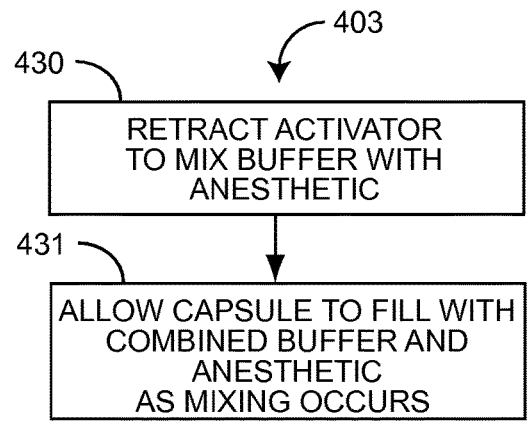
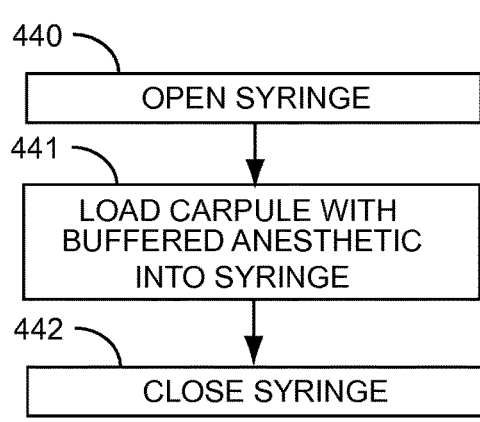
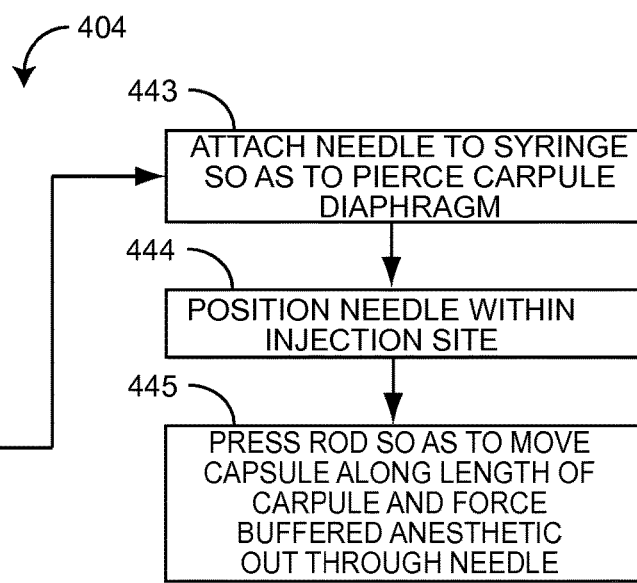
FIG. 4A
FIG. 4B
FIG. 4C
FIG. 4D

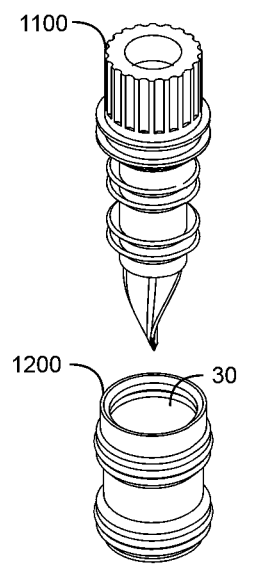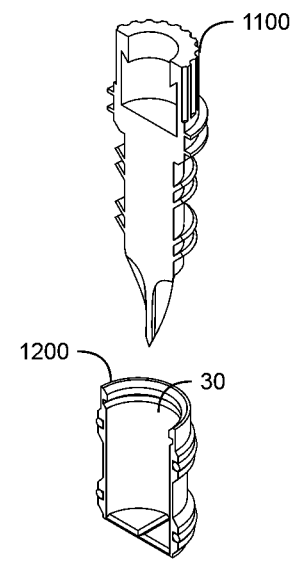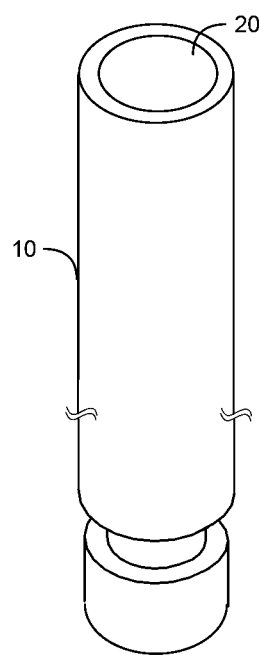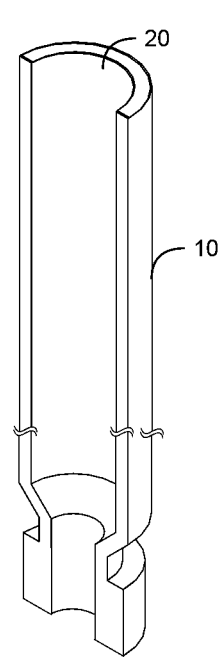
FIG. 6A        FIG. 6B

DENTAL ANESTHETIC BUFFER SYSTEM

CROSS-REFERENCE TO RELATED APPLICATIONS

The present application claims priority benefit under 35 U.S.C. § 119(e) to U.S. Provisional Patent Application Ser. No. 61/954,628, filed Mar. 18, 2014, titled Dental Anesthetic Buffer System, hereby incorporated in its entirety by reference herein.

BACKGROUND OF THE INVENTION

Dentists often inject an anesthetic into a patient's gums prior to performing various procedures, such as drilling cavities, preparing teeth for crowns and tooth extractions, to name a few. FIGS. 1A-D illustrate prior art anesthetic carpule 110, empty dental syringe 130, needle 160 and injected syringe 170. As shown in FIG. 1A, a carpule 110 has a glass or plastic tube 112 having an open first end 101 and an opposite open second end 102. A rubber stopper 114 seals the first end 101 and a diaphragm 115 held in place by an aluminum cap 116 seals the second end 102. An anesthetic 118 is contained in the tube 112 between the sealed ends 101, 102. An aperture 117 in the cap 116 allows needle access to the anesthetic 118 via a punctured hole in the diaphragm 115.

As shown in FIGS. 1B-D, the carpule 110 is loaded into a syringe 130 for injection (FIG. 1B). A needle 160 is inserted through the diaphragm 115 and held in place with a needle cap 164 pressed over a threaded syringe port 133 (FIG. 1C). A rod 134 engages the rubber stopper 114 via a harpoon 152 piercing the exposed end of the stopper 114. The rod 134 is used to eject any air from the needle prior to insertion of the needle 162 into a patient tissue site. The harpoon 152 allows the rod 134 to slightly withdraw the stopper so as to aspirate the syringe, insuring the needle is not in a blood vessel. At that point, the rod 134 drives the rubber stopper down the carpule, injecting the contents into the tissue site (FIG. 1D).

SUMMARY OF THE INVENTION

Numbing solutions, such as lidocaine, sting when injected, due to a low (acidic) pH. In order to reduce the sting of a dental anesthetic, a buffering solution, such as sodium bicarbonate, can be mixed into the anesthetic prior to injection so as to raise the pH (lower the acidity) of the anesthetic. This reduces injection pain and allows the anesthetic to take effect quicker. The buffer also ionizes the anesthetic molecules so that they immediately act on a patient's nerve cells. Further, the reaction produces carbon dioxide, which adds to the anesthetic effect. The buffered solution is then injected using a standard dental syringe. In an embodiment, the buffer is sodium bicarbonate. In an embodiment, the buffer system mixes 0.17 ml of sodium bicarbonate with the anesthetic.

A dental anesthetic buffer system advantageously replaces the rubber stopper in a standard anesthetic carpule so as to provide a self-buffering carpule that is activated prior to insertion into a syringe. In various embodiments, the buffer system delivers the buffer by activating a knob protruding from the carpule. This causes the buffer to be released into the carpule and mixed with the anesthetic prior to injection.

The exact measurements for buffer per anesthetic carpule is dependant on the concentration of the acid solution that the anesthetic is dissolved in. For lidocaine and perhaps Mapivacaine and carbocaine, the amount of 8.4% solution of sodium bicarbonate needed to buffer the acid solution is 0.17 ml per 1.7 ml of anesthetic. Any variation in acid molarity can be handled by either increasing or decreasing the concentration of the sodium bicarbonate to buffer the solution completely without changing the volume of buffer from 0.17 ml.

There is a delay after the anesthetic and buffer solutions are mixed until full buffering is achieved. In an embodiment, a small vibrating container may be used after activation to speed the mixing process. In an embodiment, a buffered carpule is vibrated for 5-8 seconds to complete the mixing process.

Advantageously, an anesthetic buffer system described herein does not need a special carpule so that dentists and other potential users may use the system with minimal change of procedure or product look and feel. In an embodiment, a plastic carpule of the same dimensions as a glass carpule is utilized. The materials used for the plunger and fluid holder are medical grade plastic. The diaphragm is rubber. No special shipping considerations are need for the buffering system other than providing a safe packaging system so that the glass carpule does not break during shipping. Packaging methods may range from a plastic flat container that holds carpules in a row or a tin can that holds 50 carpules next to each other.

One aspect of a dental anesthetic buffer system is a carpule having a first end and a second end, a capsule at least partially disposed within the carpule proximate the first end so as to fluidly seal the first end, and a diaphragm disposed proximate the second end so as to fluidly seal the second end. A liquid anesthetic is contained within the carpule between the first end and the second end. A liquid buffer is contained within the capsule. An activator is disposed proximate the buffer and extending from the carpule first end. The activator is actuated so as to move the activator from a first position to a second position. The activator second position releases the buffer from the capsule and combines the buffer with the anesthetic.

Another aspect of a dental anesthetic buffer system is providing a carpule having a sealed first end and an open second end, disposing an anesthetic within the carpule, sealing the open second end with a capsule and sealing a buffer within the capsule. The capsule is activated so as release the buffer into the anesthetic.

A further aspect of a dental anesthetic buffering system is a carpule means for containing an anesthetic between a first end and a second end, a capsule means for containing a buffer and sealing the first end, and a diaphragm means for sealing the second end. An activator means combines the buffer and the anesthetic into a buffered anesthetic. A needle pierces the diaphragm means and provides a conduit for the buffered anesthetic. An injection means forces the buffered anesthetic through the needle means.

BRIEF DESCRIPTION OF THE DRAWINGS

FIGS. 4A-D are flow diagrams for advantageous dental anesthetic fabricating, buffering and injecting methods;

FIGS. 6A-B are exploded perspective and cutaway exploded perspective views, respectively, of an advancing-activator;

DETAILED DESCRIPTION OF THE PREFERRED EMBODIMENTS

Figures 2A, 2B, 2C:
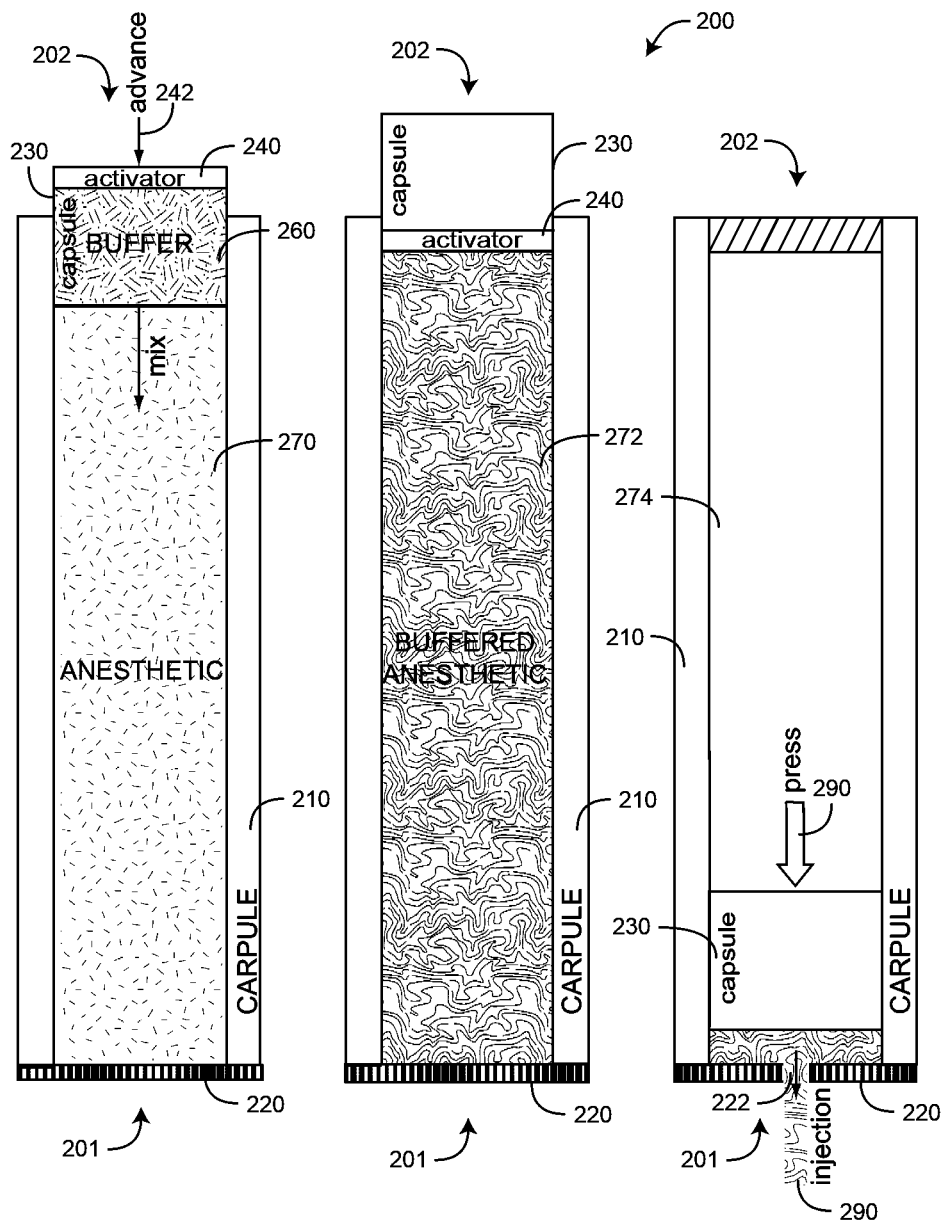
FIGS. 2A-C are partial-cutaway side views of an advantageous dental anesthetic buffer system having an advancing activator.

FIGS. 2A-C illustrate an advantageous dental anesthetic buffer system 200 having an advancing activator. As shown in FIG. 2A, the buffer system has a carpule 210 sealed at a first end 201 with a typically rubber diaphragm 220. The carpule 210 is sealed at a second end 202 with a capsule 230 containing a buffer 260. The carpule 210 contains an anesthetic 270 between the two seals 220, 230. When a patient is ready to be injected with the anesthetic, the activator 240 is advanced 242 inside the capsule 230, which pushes the buffer 260 from the capsule 230 so as to mix the buffer 260 with the anesthetic 270. In an embodiment, advancing the activator 240 breaks a capsule seal, allowing the activator 240 to push the buffer from capsule 230.

Figure 1A:
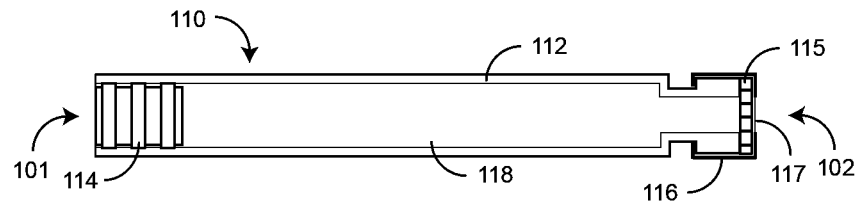
FIGS. 1A-D are side, perspective loading, side pre-injection and side injection views, respectively, of a prior art carpule and corresponding dental syringe and needle.
Figure 1B:
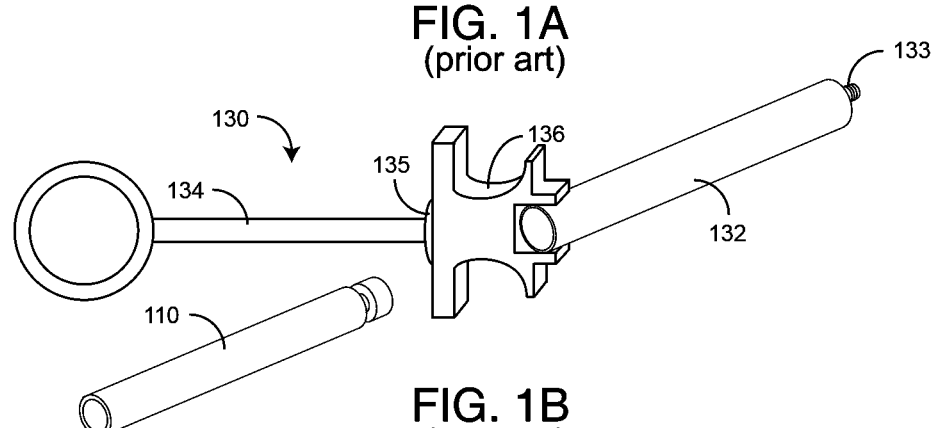
Figure 1C:
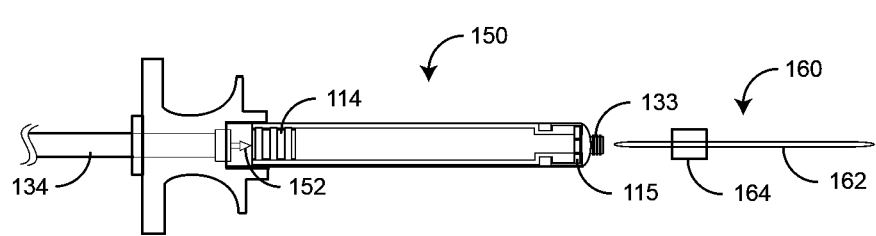

As shown in FIG. 2B, the buffered anesthetic 272 is the combined volume of the anesthetic 270 and buffer 260. This larger volume of buffered anesthetic 272 partially pushes the capsule 230 from the second end 202. The capsule 230 is advantageously designed to accommodate the increased volume of liquid between the diaphragm 220 and the capsule 230 while maintaining the seal at the carpule second end 202. At this stage, the carpule 210 may be shaken or vibrated by hand or machine for a short period to insure that the buffered anesthetic is completely mixed and has had time to chemically stabilize. Once the buffered anesthetic is fully mixed and stabilized, the carpule is loaded into syringe, such as shown and described with respect to FIG. 1B, above. A needle is fitted to the syringe, which pierces the diaphragm 220, such as shown and described with respect to FIG. 1C, above. The harpoon at the end of the syringe rod engages the capsule 230, and, after aspiration, the rod is pressed 290, which advances the capsule 230 the length of the carpule 210 and injects 290 the buffered anesthetic 272 into a patient via a needle (not shown) protruding into the carpule via the diaphragm puncture 222.

Figures 3A, 3B, 3C:
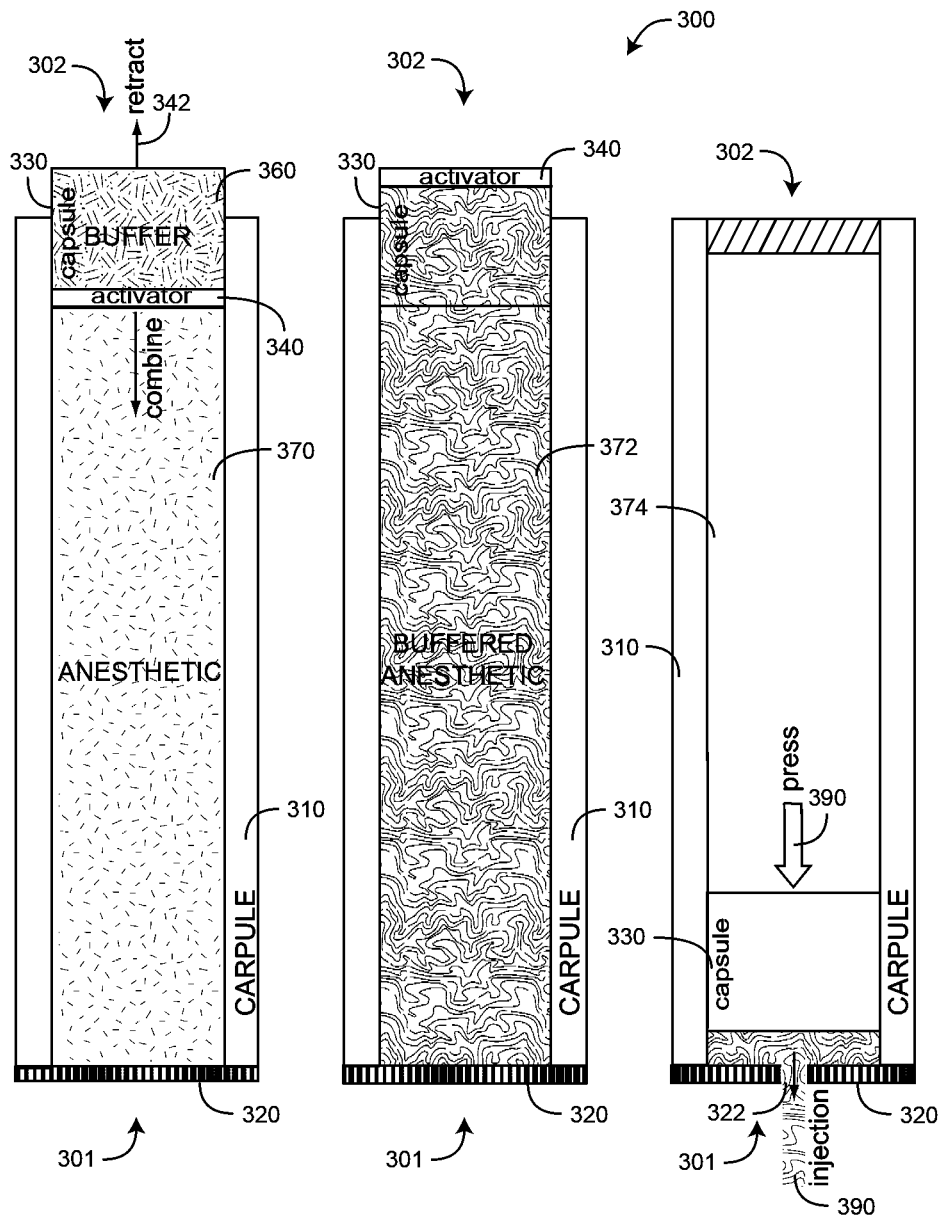
FIGS. 3A-C are partial-cutaway side views of an advantageous dental anesthetic buffer system having a retracting activator.

FIGS. 3A-C illustrate an advantageous dental anesthetic buffer system 300 having a retracting activator. As shown in FIG. 3A, the buffer system has a carpule 310 sealed at a first end 301 with a typically rubber diaphragm 320. The carpule 310 is sealed at a second end 302 with a capsule 330 containing a buffer 360. The carpule 310 contains an anesthetic 370 between the two seals 320, 330. When a patient is ready to be injected with the anesthetic, the activator 340 is retracted 342 inside the capsule 330, which extrudes the buffer 360 from the capsule 330 into carpule 310 and also draws the anesthetic 370 into the capsule 330. In an embodiment, an activator aperture (not shown) is opened or otherwise unsealed so as to allow the buffer 360 and the anesthetic 370 to mix between the carpule 310 and the capsule 330. Prior to activation, the activator aperture is closed or otherwise sealed.

As shown in FIG. 3B, the buffered anesthetic 372 is the combined volume of the anesthetic 370 and buffer 360. Advantageously, this larger volume of buffered anesthetic 372 fills both the capsule 330 and the carpule 310. At this stage, the carpule 310 may be shaken or vibrated by hand or machine for a short period to insure that the buffered anesthetic is completely mixed and has had time to chemically stabilize. Once the buffered anesthetic is fully mixed and stabilized, the carpule is loaded into a syringe, such as shown and described with respect to FIG. 1B, above. A needle is fitted to the syringe, which pierces the diaphragm 320, such as shown and described with respect to FIG. 1C, above. The harpoon at the end of the syringe rod engages the capsule 330, and, after aspiration, the rod is pressed 390, which advances the capsule 330 the length of the carpule 310 and injects 390 the buffered anesthetic 372 into a patient via a needle (not shown) protruding into the carpule via the diaphragm puncture 322.

FIGS. 4A-D illustrate advantageous dental anesthetic carpule manufacturing, buffering and injecting methods 401-404. As shown in FIG. 4A, in a carpule manufacturing method 401, a hollow tube is fabricated to fit within a standard dental syringe 410. A capsule and corresponding activator are fabricated to fit within the tube 411. The needle-end of the tube is sealed with a diaphragm 412. The tube is prefilled with an anesthetic 413. The capsule is prefilled with a buffer 414. One end of the tube is sealed with the buffer-filled capsule 415.

As shown in FIG. 4B, in a dental anesthetic carpule buffering method 402, an activator is advanced to mix a buffer with an anesthetic 420. A capsule previously containing the buffer and sealing one end of a carpule is allowed to partially retract from the carpule as mixing of the buffer and the anesthetic occurs 421.

As shown in FIG. 4C, in another dental anesthetic carpule buffering method 403, an activator is retracted to mix a buffer with an anesthetic 430. A capsule previously containing the buffer and sealing one end of a carpule is allowed to fill with the buffered anesthetic as mixing of the buffer and the anesthetic occurs 431.

As shown in FIG. 4D, in a dental buffered anesthetic injection method 404, a dental syringe is opened 440. A carpule containing a buffered anesthetic (see FIGS. 4B-C) is loaded into the syringe 441, and the syringe is closed 442. A needle is attached to the syringe so as to pierce the carpule diaphragm and extend into the buffered anesthetic solution. The dental practitioner forces some solution out of the needle to rid the carpule and needle of air, and positions the needle within an injection site of a patient's gums 444. The dental practitioner aspirates the syringe to insure the needle tip is not positioned in an artery, and then presses the syringe rod so as to move the capsule along the length of the carpule 445. This forces buffered anesthetic out through the needle and into the injection site 445.

FIGS. 5-12 illustrate an advancing-activator embodiment of a dental anesthetic buffering system. FIGS. 5A-B illustrates an advancing-activator carpule 500. The advancing-activator carpule 500 is supplied to dental professionals with a glass or plastic tube 10 filled with an anesthetic. A carpule first end 51 is terminated with a conventional diaphragm held in place with an aluminum cap. A carpule second end 52 is advantageously terminated with an advancing-activator capsule 510 containing a buffer. A liquid anesthetic 20 is thereby sealed between the diaphragm (not shown) and the capsule 510.

As shown in FIGS. 5-12, the capsule 510 has a first position 501 (FIG. 5A) having a buffer contained within a fluid holder 1200 and a plunger 1100 partially disposed within the fluid holder 1200 so as to seal a buffer within the fluid holder 1200. The capsule 510 has a second position 502 (FIG. 5B) with the plunger 1100 substantially disposed within the fluid holder 1200 so that a plunger spear tip 1120 pierces a fluid holder bottom 1220 as it forces the buffer out of the fluid holder 1200 and into the anesthetic 20.

Figure 1D:
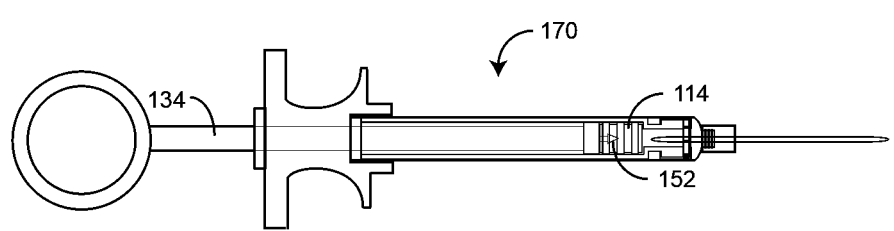

Also shown in FIGS. 5-12, the capsule 510 is activated to release a buffer into the anesthetic by forcing the knob 1110 (FIGS. 11A-B) at a protruding end of the capsule 510 so that the spear tip 1120 (FIGS. 11A-B) pierces the capsule bottom 1220. For example, a dentist may hold the carpule 500 with the knob end down and rap the knob on a hard surface so as to force the plunger 1100 from the first position 501 (FIG. 5A) to the second position 502 (FIG. 5B). After the buffer is released into the anesthetic and the carpule is loaded into a syringe, the capsule functions similarly to a conventional rubber stopper. In particular, the knob aperture 1150 (FIGS. 11A-B) may be filled with a liquid rubber that hardens so as to receive a syringe barb 152 (FIGS. 1C-D) at the end of a syringe rod 134. The rod then presses the capsule 510 down the length of carpule tube 10 (FIGS. 5A-B) so as to expel the buffered anesthetic from the carpule, through an attached needle and, typically, into a dental patient's gums prior to a dental procedure.

FIGS. 6-10 further illustrate an advancing-activator capsule 510 having a plunger 1100 (FIGS. 6A-B) and a fluid holder 1200 (FIGS. 6A-B). As shown in FIGS. 7A-B, the fluid holder 1200 is disposed at one end of the tube 10 so as to seal an anesthetic within the tube. The fluid holder 1200 is filled with a buffer. As shown in FIGS. 8A-B, in a first capsule position, the plunger 1100 is partially disposed into the fluid holder 1200 so as to seal the buffer within the fluid holder 1200. As shown in FIGS. 9A-B, in a second capsule position, the plunger 1100 is forced further into the fluid holder 1200 so that the plunger spear-tip 1120 (FIGS. 11A-B) breaks through the fluid holder scored-bottom 1220, 1222 (FIGS. 12A-B). As shown in FIGS. 10A-B, as buffer from the fluid holder 1200 flows into the anesthetic in the tube 10, the tube volume of anesthetic plus buffer increases. Advantageously, as the tube fluid volume 20 increases, the capsule 1100, 1200 rises from a first position (FIG. 10A) with the top of the fluid holder 1200 proximately flush with the top of the tube 10 to a second position (FIG. 10B) with the top of the fluid holder 1200 extending from the top of the tube 10, so as to accommodate the buffered anesthetic volume.

Figures 5A, 5B:
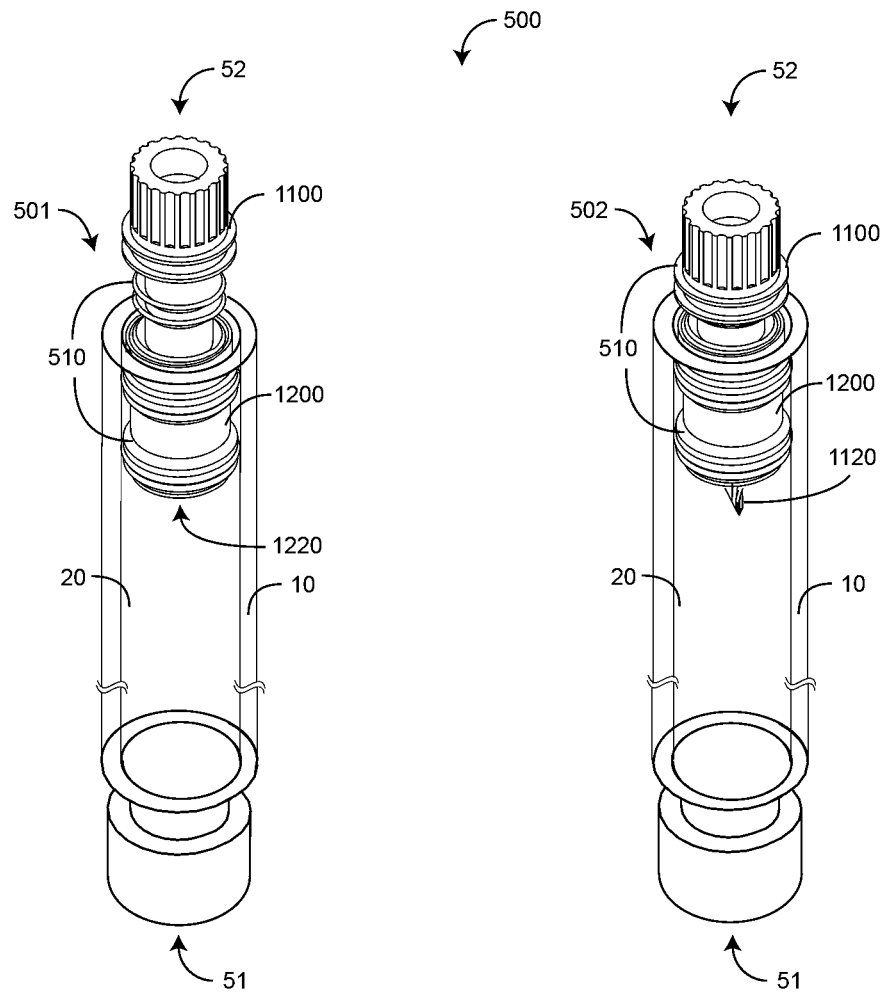
FIGS. 5A-B are pre-activated and post-activated perspective views, respectively, of a dental anesthetic buffering system embodiment having an advancing-activator.
Figures 7A, 7B:
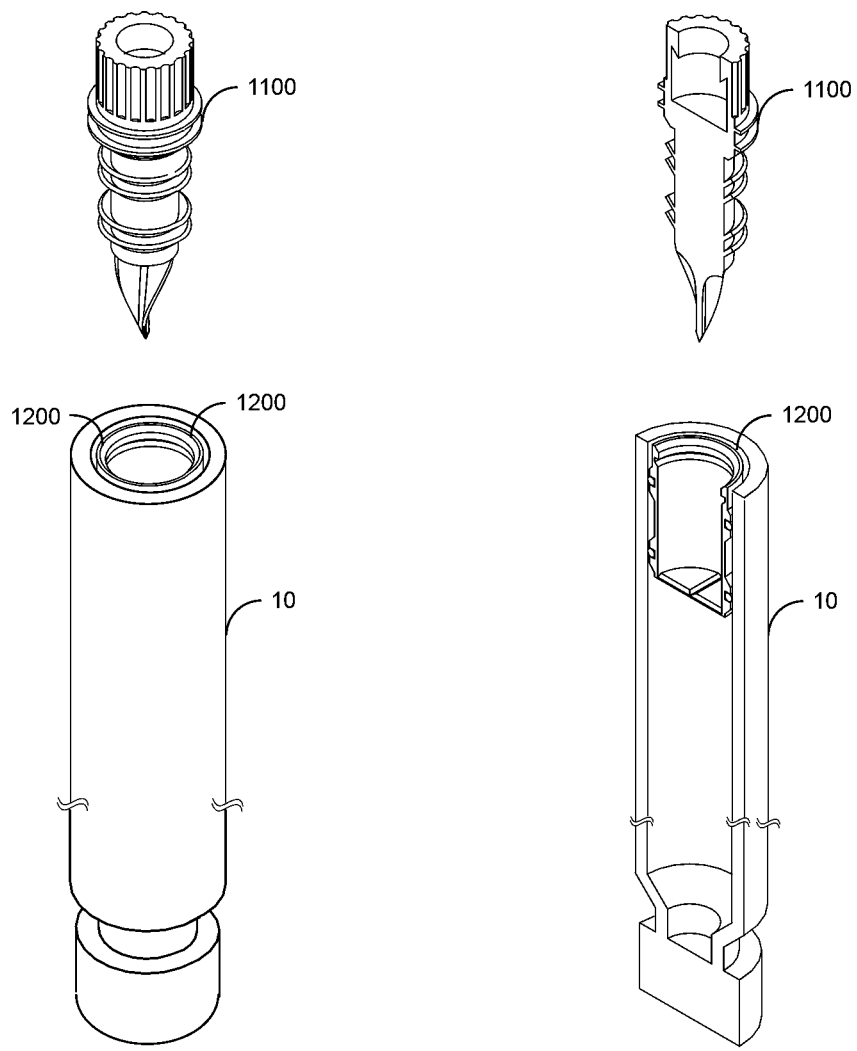
FIGS. 7A-B are partially-exploded perspective and cutaway partially-exploded perspective views, respectively, of an advancing-activator.
Figures 8A, 8B:
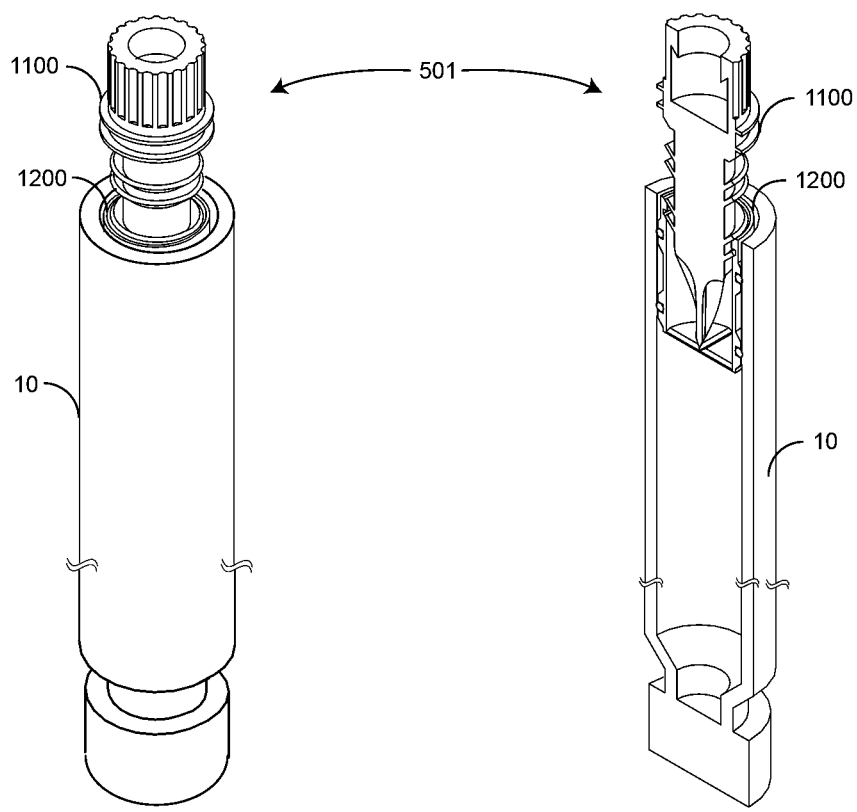
FIGS. 8A-B are perspective and cutaway perspective views, respectively, of an advancing-activator in a pre-activated position.
Figures 9A, 9B:
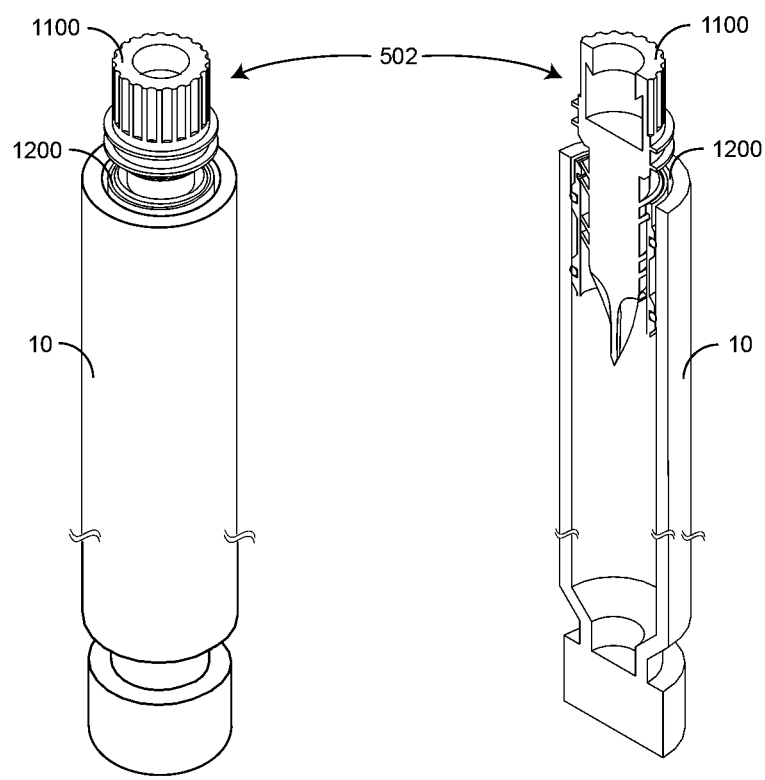
FIGS. 9A-B are perspective and cutaway perspective views, respectively, of an advancing-activator in a post-activated position.
Figure 10A:
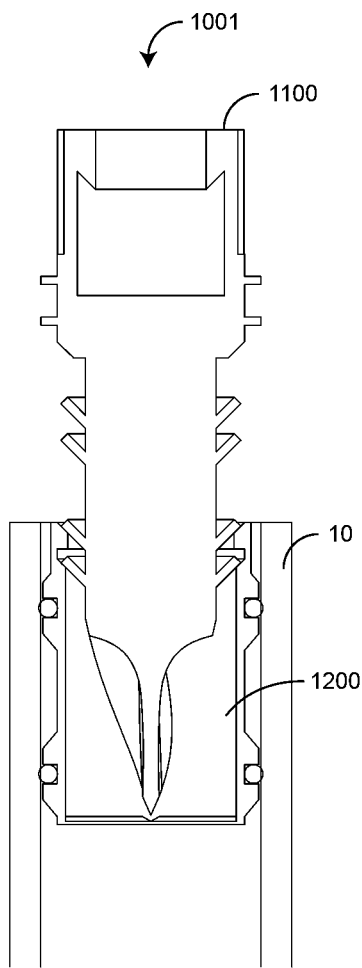
FIGS. 10A-B are pre-activated and post-activated cutaway side views, respectively, of an advancing-activator.
Figure 10B:
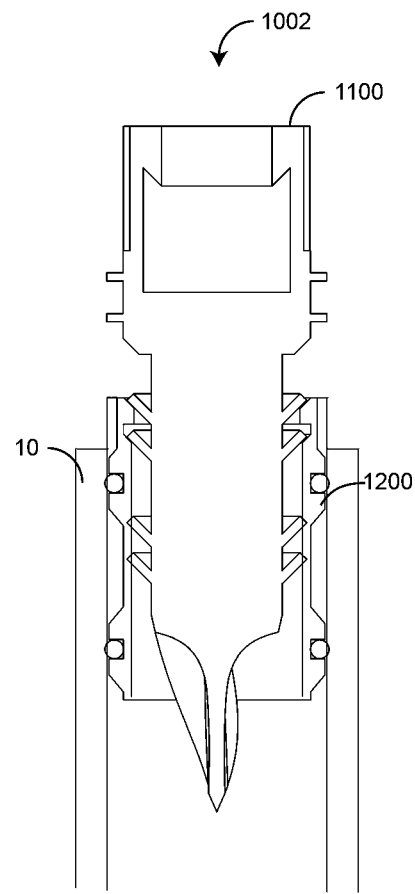
Figure 11A:
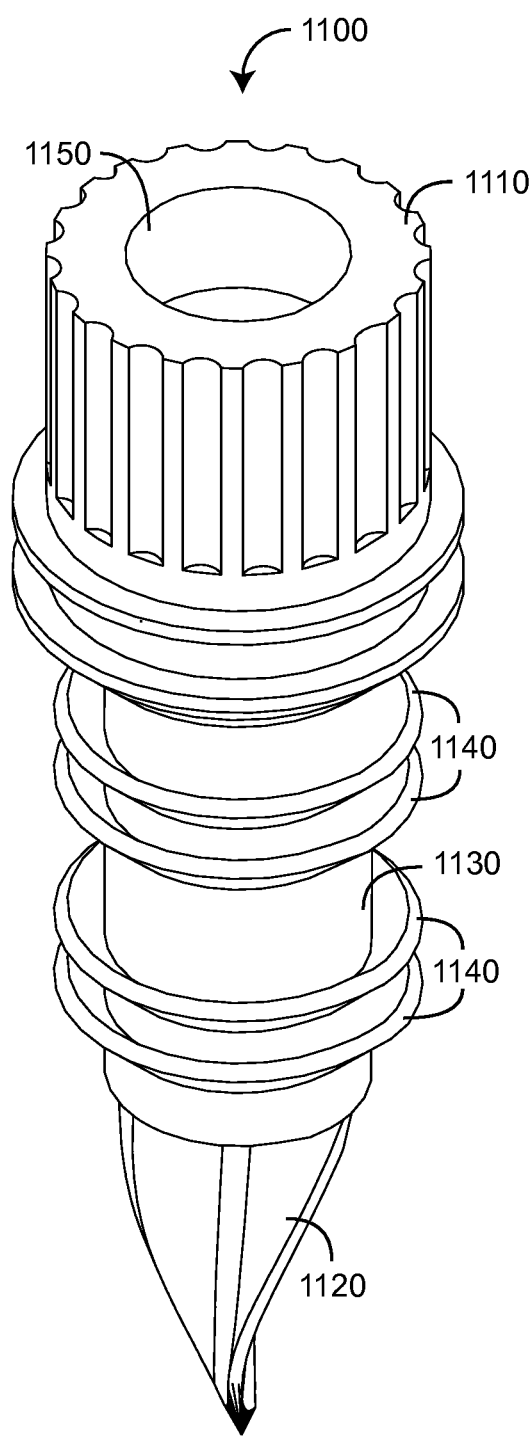
FIGS. 11A-B are perspective and cutaway perspective views, respectively, of a plunger embodiment.
Figure 11B:
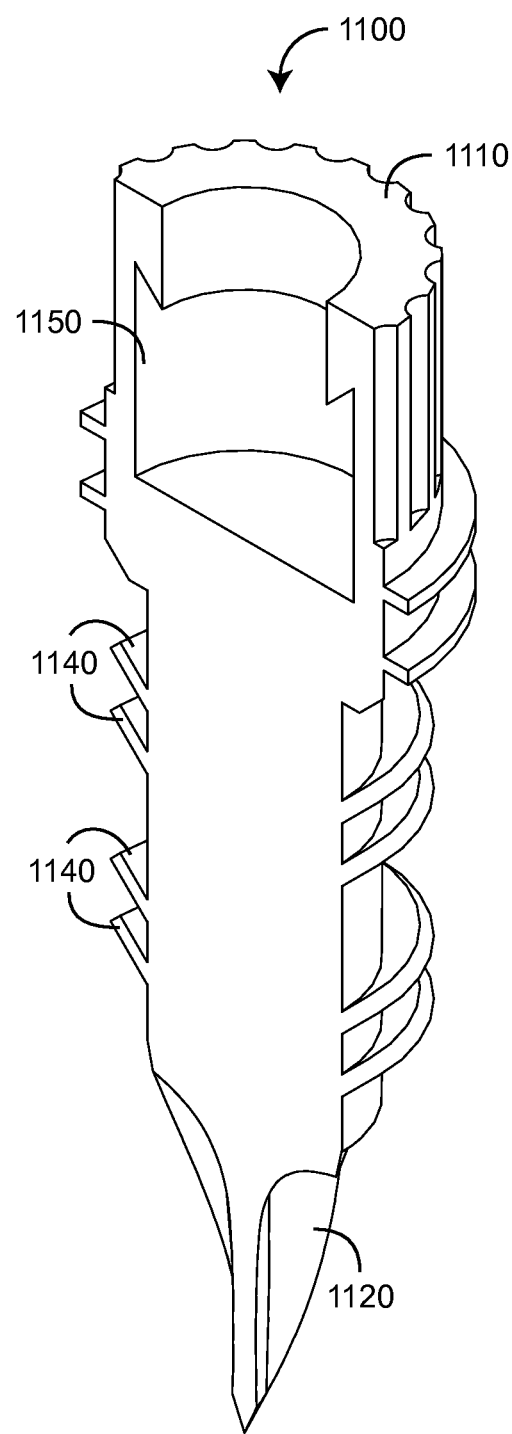
Figures 12A, 12B:
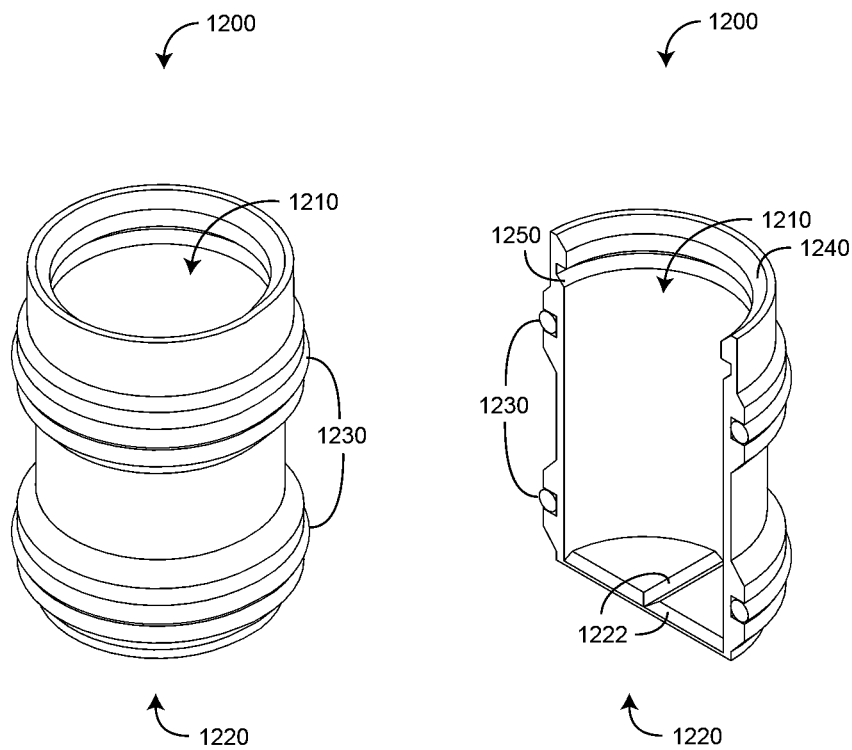
FIGS. 12A-B are perspective and cutaway perspective views, respectively, of a buffer container embodiment.

FIGS. 11A-B illustrate a plunger 1100 embodiment of an advancing-activator capsule 510 (FIGS. 5A-B). The plunger 1100 has a knurled knob 1110, a spiral spear tip 1120, a generally-cylindrical shaft 1130, semi-flexible flanges 1140 and an knob aperture 1150. The knob 1110 is disposed at a first plunger end so as to receive the end of a syringe rod. In an embodiment, the aperture 1150 is rubber-filled so as to receive a rod barb. The spear-tip 1120 is disposed at a second plunger end opposite the first plunger end. The shaft 1130 is disposed between the plunger ends and supports generally circular flanges 1140 extending from the shaft at an angle away from the spear-tip 1120. Advantageously, the flanges 1140 are releasably captured by a fluid holder groove 1250 having an angle toward the fluid holder bottom 1220 so as to resist fluid pressure tending to push the plunger from the fluid holder.

FIGS. 12A-B illustrate a fluid holder 1200 embodiment of an advancing-activator capsule 510 (FIGS. 5A-B). The fluid holder 1200 has an open top 1210 and a closed bottom 1220. The bottom 1220 is advantageously scored 1222 so that the plunger spear-tip can break-open and extend through the bottom 1220 and release buffer fluid from the container volume. A groove 1250 is disposed around the inside perimeter of the fluid holder 1200 so as to capture the plunger flanges 1140 (FIGS. 11A-B). The groove 1250 advantageously faces toward the fluid holder bottom 1220 so as to resist movement of the plunger out of the fluid holder open top 1210. In a glass tube embodiment, washers 1230 disposed around the fluid holder outside perimeter accommodate irregularities in the glass tube interior. In a plastic tube embodiment, the washers 1230 may be unneeded as tube irregularities as less common.

Figure 13:
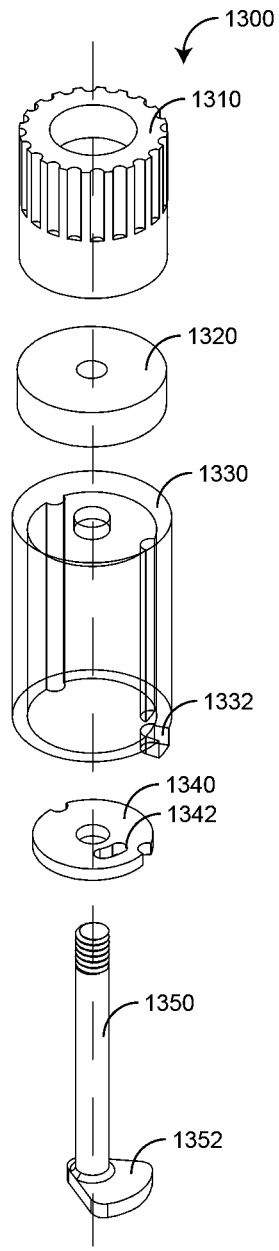
FIG. 13 is an exploded view of a retracting-activator.
Figure 14A:
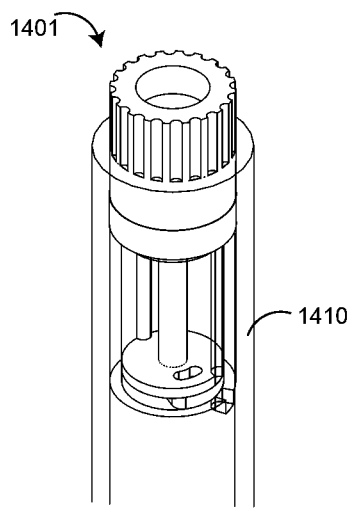
FIGS. 14A-D are pre-activated, activating and post-activated perspective views, respectively, of a dental anesthetic buffering system embodiment having a retracting-activator.
Figure 14B:
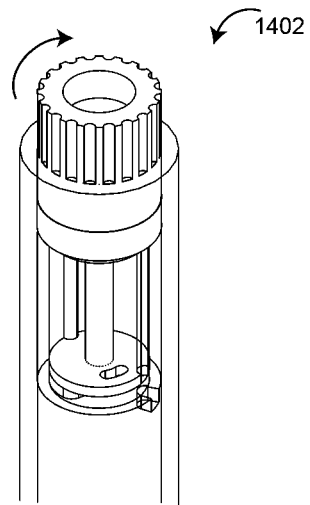
Figure 14C:
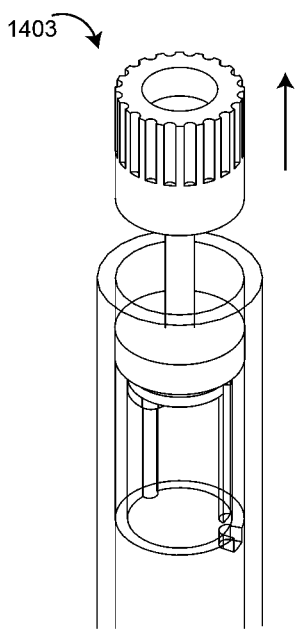
Figure 14D:
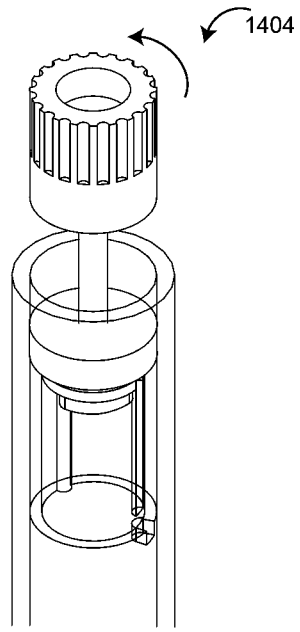

FIG. 13 illustrates a retracting-activator embodiment of a dental anesthetic buffering system 1300, including an activator knob 1310, a silicon washer 1320, a housing 1330, a slotted stopper 1340 and a cam shaft 1350. The knob 1310 is rotatably connected to the cam shaft 1350, which extends into the housing 1330. The washer 1320 is installed between the knob 1310 and the housing 1330. The slotted stopper 1340 is installed within the housing 1330 between the cam shaft 1350 and the cam shaft cam 1352. The housing 1330 is configured to contain a buffer solution. The slotted stopper 1340 has a slot 1342 that provides a buffer flow path from the housing 1330 into the carpule 1410 (FIG. 14A). The buffer flow path is blocked by the cam 1352 until the cam shaft 1350 is rotated away from the stopper slot 1342. This allows the buffer to flow from the housing 1330 into the carpule 1410 so as to mix with the anesthetic.

As shown in FIG. 13, the ribbed knob 1310 (is screwed into the plunger 1350 with a screw orientation that tightens as the ribbed handle turns clockwise. This assures that during activation (clockwise turning) the ribbed handle and the cam handle do not come apart. The cam will be in a position under the slot of the free sliding stopper at the bottom of the buffer system FIG. 14A. The silicone washer 1320 sits between the bottom of the ribbed knob 1310 and the top of the buffer housing 1330. This seals the buffer housing 1330 and also prevents the knob 1310 from being pushed closer to the buffer housing 1330 at any point so as to prevent inadvertent disassembly of the free floating stopper 1340 from the housing 1330 bottom.

Also shown in FIG. 13, below the silicone washer 1320 is the buffer housing 1330. In an embodiment, housing 1330 contains 0.17 ml of liquid by volume when filled and the cam 1352 is in a closed position under the stopper slot 1342. The housing 1330 has two ridges that act like rails for the stopper 1340 to travel up and down on. This assures that the stopper 1340 does not rotate during operation, which may interfere with opening and closing the housing with the rotation of the cam 1352.

In an embodiment, the cam 1352 is ½ mm wider on both ends than the stopper slot 1342 to allow for a proper seal in the closed position (FIG. 14A). The cam 1352 is also beveled on the bottom so as to lock in the closed position between a housing ledge 1332 and the rails, squeezing tightly against the stopper 1340. The stopper 1340 provides opposite pressure against the cam 1352 due to the buffer liquid behind it.

FIGS. 14A-D illustrate pre-activated 1401, activating 1402, mixing 1403 and post-activated 1404 positions so as to mix a buffer solution into an anesthetic. In a pre-activated position 1401, the cam 1352 (FIG. 13) is locked proximate the stopper slot 1342 (FIG. 13). In an open position 1402, with a clockwise-rotated knob, the buffer is allowed to flow through the stopper slot and into the carpule 1410. In a mixing position 1403, raising the knob pulls-up the stopper so as to force the buffer through the stopper slot and into the carpule. In a reclosed position 1404, a counterclockwise-rotated knob recloses the stopper slot. The whole buffering system 1300 (FIG. 13) is then pushed into the carpule 1410 using a regular anesthetic syringe, until the anesthetic is injected into the area needed. The ribbed knob 1310 (FIG. 13) is hollow at the top and filled with silicone. This allows the harpoon of the anesthetic syringe to imbed into the knob. This also allows the doctor to apply negative pressure during anesthetic aspiration so as to verify the needle is not placed inside a blood vessel. A ledge on the inside of the knob hollow area prevents the silicone from coming out when the doctor aspirates.

A dental anesthetic buffer system has been disclosed in detail in connection with various embodiments. These embodiments are disclosed by way of examples only and are not to limit the scope of the claims that follow. One of ordinary skill in the art will appreciate many variations and modifications.

What is claimed is:

1. A dental anesthetic buffering method comprising:
   providing a carpule having a sealed first end and an open second end;
   disposing an anesthetic within the carpule;
   sealing the open second end with a capsule;
   sealing a buffer within the capsule; and
   activating the capsule so as release the buffer into the anesthetic prior to insertion into a syringe.

2. The dental anesthetic buffering method according to claim 1 wherein sealing the buffer within the capsule comprises disposing an activator at least partially within the capsule.

3. The dental anesthetic buffering method according to claim 2 wherein activating the capsule comprises advancing the activator within the capsule.

4. The dental anesthetic buffering method according to claim 3 wherein advancing the activator within the capsule comprises:
   forcing a plunger into the capsule; and
   breaking a bottom portion of the capsule with a spear tip end of the plunger so that the buffer flows from the capsule bottom portion into the anesthetic.

5. The dental anesthetic buffering method according to claim 2 wherein activating the capsule comprises at least partially retracting the activator from the capsule.

6. The dental anesthetic buffering method according to claim 5 wherein at least partially retracting the activator from the capsule comprises rotating a knob portion of the activator from a first position blocking a slotted stopper to a second position unblocking the slotted stopper.

7. The dental anesthetic buffering method according to claim 6 wherein at least partially retracting the activator from the capsule comprises at least partially pulling the knob from the capsule so as to slidably move the slotted stopper within the capsule so that buffer flows from the capsule through the slotted stopper and into the anesthetic.

* * * * *